United States Patent [19]
Hoogeboom

[11] Patent Number: 5,928,263
[45] Date of Patent: Jul. 27, 1999

[54] SURGICAL INSTRUMENT WITH FLEXIBLE ACTUATOR AND RIGID ACTUATOR COVER

[75] Inventor: Thomas J. Hoogeboom, Portage, Mich.

[73] Assignee: Aslan Medical Technologies, Kalamazoo, Mich.

[21] Appl. No.: 09/017,434

[22] Filed: Feb. 2, 1998

[51] Int. Cl.⁶ .................................................. A61B 17/28
[52] U.S. Cl. ......................... 606/205; 606/204; 606/206; 606/210; 606/180
[58] Field of Search ................... 606/205, 180, 606/206, 204, 210

[56] References Cited

U.S. PATENT DOCUMENTS

| | | |
|---|---|---|
| 1,519,938 | 12/1924 | Smith . |
| 1,532,020 | 3/1925 | Angelides . |
| 1,616,121 | 2/1927 | Gruber . |
| 2,137,710 | 11/1938 | Anderson . |
| 2,518,994 | 8/1950 | Miller . |
| 2,989,334 | 6/1961 | Browne . |
| 3,146,015 | 8/1964 | Roberge . |
| 3,265,429 | 8/1966 | Shatt . |
| 4,393,872 | 7/1983 | Reznik et al. . |
| 4,644,651 | 2/1987 | Jacobsen . |
| 4,662,371 | 5/1987 | Whipple et al. . |
| 4,760,848 | 8/1988 | Hasson . |
| 4,872,456 | 10/1989 | Hasson . |
| 4,898,157 | 2/1990 | Messroghli et al. . |
| 4,944,093 | 7/1990 | Falk . |
| 4,944,741 | 7/1990 | Hasson . |
| 5,002,554 | 3/1991 | Korber . |
| 5,009,661 | 4/1991 | Michelson . |
| 5,089,007 | 2/1992 | Kirsch et al. . |
| 5,152,780 | 10/1992 | Honkanen et al. . |
| 5,217,464 | 6/1993 | McDonald . |
| 5,282,817 | 2/1994 | Hoogeboom et al. . |
| 5,352,223 | 10/1994 | McBrayer et al. ................... 606/205 |
| 5,355,871 | 10/1994 | Hurley et al. ...................... 606/205 |
| 5,370,658 | 12/1994 | Scheller et al. .................... 606/205 |
| 5,470,328 | 11/1995 | Furnish et al. . |
| 5,498,256 | 3/1996 | Furnish . |
| 5,501,698 | 3/1996 | Roth et al. ........................ 606/205 |
| 5,618,306 | 4/1997 | Roth et al. ........................ 606/205 |
| 5,634,918 | 6/1997 | Richards ........................... 606/205 |
| 5,665,105 | 9/1997 | Furnish et al. .................... 606/205 |

FOREIGN PATENT DOCUMENTS

WO8103122 of 0000 WIPO .

Primary Examiner—Michael Buiz
Assistant Examiner—(Jackie) Tan-Uyen Thi Ho
Attorney, Agent, or Firm—Price, Heneveld, Cooper, Dewitt & Litton

[57] ABSTRACT

A surgical instrument includes an elongate tubular member, an end effector at the distal end of the tubular member, a linkage rod slidably disposed within the tubular member, a distal connector fixed to the proximal end of the tubular member, a proximal connector fixed to the proximal end of the linkage rod, at least one resiliently flexible actuating member, and a lever pivotally to the proximal connector. The lever generally overlies and contacts the actuator member. Pivoting of the lever toward the flexible actuator member causes the linkage rod to move a movable jaw of the end effector. The surgical instrument has a relatively larger actuator surface for easier manipulation, and better balance. The actuator member also has a point of maximum leverage closer to the distal end, than other surgical instruments of the same general type.

8 Claims, 3 Drawing Sheets

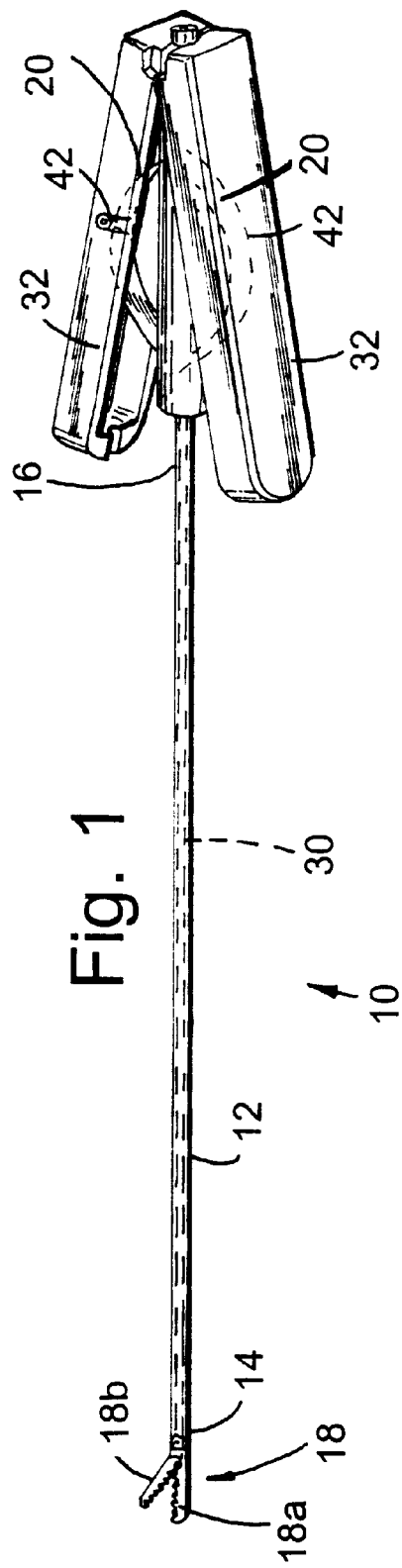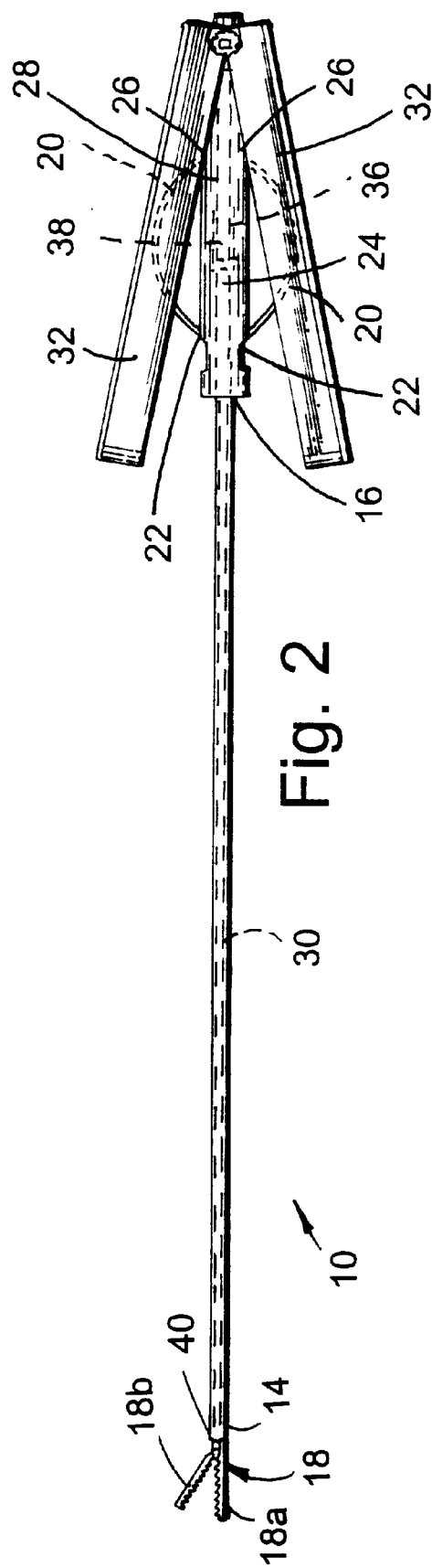

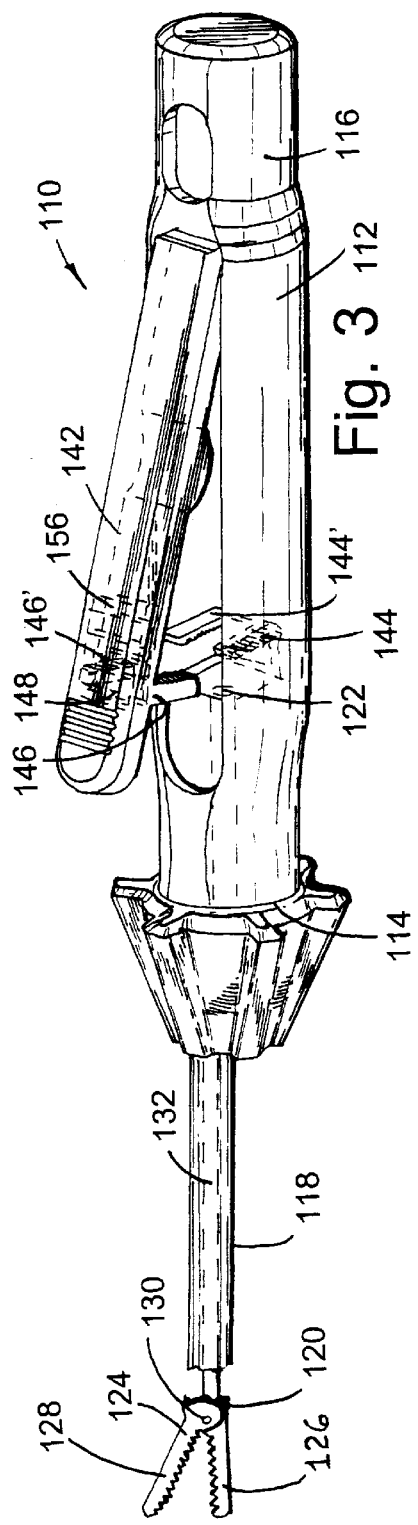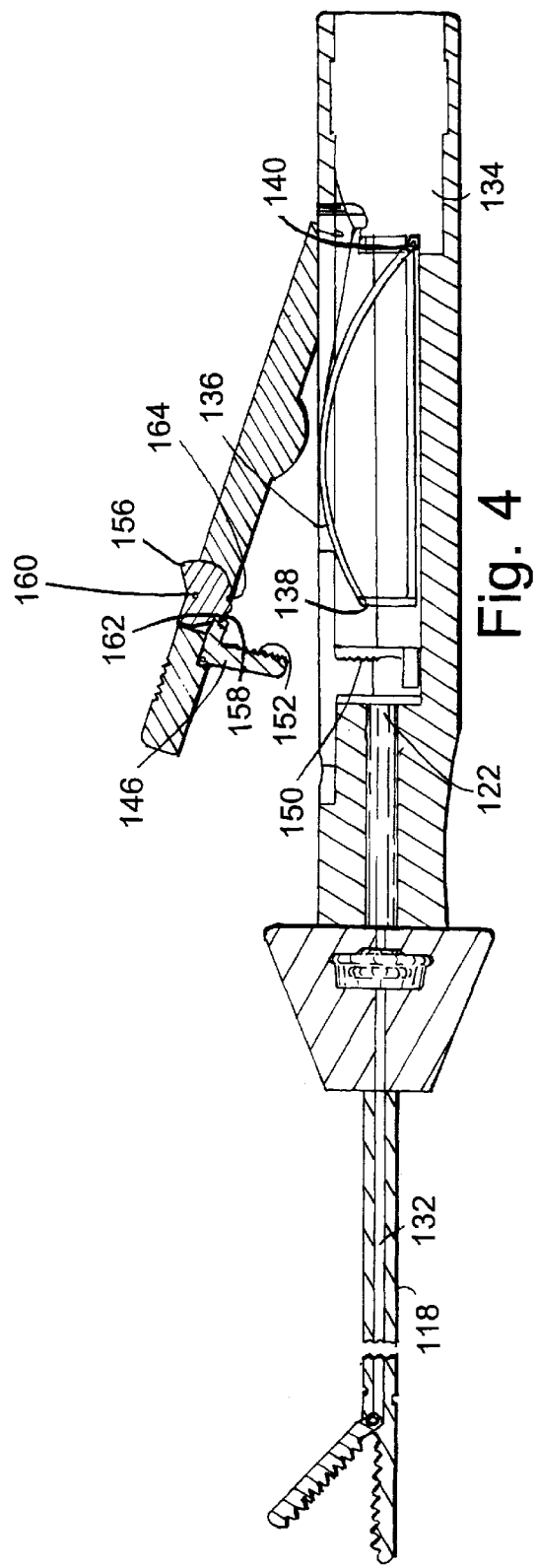

5,928,263

SURGICAL INSTRUMENT WITH FLEXIBLE ACTUATOR AND RIGID ACTUATOR COVER

FIELD OF THE INVENTION

This invention relates generally to the field of surgical instruments for performing cutting, clamping, holding or shearing functions in surgical operations, and more particularly to surgical instruments for performing laparoscopic, endoscopic, and other delicate surgical procedures.

BACKGROUND OF THE INVENTION

My prior patent, entitled "*ACTUATING HANDLE FOR MULTI-PURPOSE SURGICAL INSTRUMENT*" (U.S. Pat. No. 5,282,817), discloses a surgical instrument which can be easily held in the hand for use in performing delicate surgery. The disclosed instrument is capable of providing enhanced control as compared with other surgical instruments of the same general type.

SUMMARY OF THE INVENTION

The invention provides a surgical instrument with a dual lever actuating mechanism which shifts the point of maximum leverage more toward the distal end as compared with other surgical instruments of the same general type, while utilizing at least one resiliently flexible opposing actuator member, which has been found to provide a simple, but reliable structure, which enables precise, one-handed manipulation of the jaws at the distal end of the instrument.

The surgical instrument generally comprises an elongate tubular member having a distal end and a proximal end, an end effector, a linkage rod having a distal end and a proximal end, a distal connector fixed to the proximal end of the tubular member, a proximal connector fixed to the proximal end of the linkage rod, at least one resiliently flexible actuator member, and a lever generally overlying and contacting the actuator member. The linkage rod is slidably positioned in the tubular member and is connected at its distal end to a movable jaw of the end effector. The linkage rod extends rearwardly through the tubular member and beyond the proximal end thereof. The distal connector and the proximal connector are configured for sliding movement relative to each other along a direction generally defined by the longitudinal axis of the tubular member. The actuator member has a distal end and a proximal end. The distal end of the actuator member is operably connected to the tubular member. The actuator member is operably connected to the tubular member and extends proximally beyond the proximal end of the tubular member. The flexible actuator member is laterally compressible toward the longitudinal axis of the linkage rod. The lever has a proximal end and a distal end. The proximal end of the lever is operably connected to the proximal connector, and the distal end of the lever extends distally and outwardly away from the longitudinal axis of the tubular member. The lever generally overlies and contacts the actuator member, whereby pivoting of the lever toward the longitudinal axis of the linkage rod causes the flexible actuator member to be compressed toward the longitudinal axis of the linkage rod, which, in turn, causes the linkage rod to move the movable jaw of the end effector.

The lever actuating mechanism shifts the point of maximum leverage more toward the distal end of the surgical instrument, as compared with other surgical instruments of the same general type. This allows the surgeon to place his hand closer to the distal end of the instrument whereby the position and orientation of the end effector can be more easily controlled, while simultaneously allowing the surgeon to easily manipulate the jaws of the end effector with very slight, low force manipulation of the levers, such as between the thumb and forefinger, which may be placed on the instrument in a pencil-like grip. Further, the lever actuating mechanism of the invention provides a relatively wider actuator surface for easier manipulation than the relatively narrow flexible actuator member which has a width which is determined by other more important design parameters, such as flexibility and springiness. The lever actuating mechanism also places more weight toward the proximal end of the instrument to provide better balance whereby the end effector can be more easily and more stably held at a desired position and orientation. Another advantage with the lever actuating mechanism is that it generally covers the resiliently flexible actuator member and shields the surgeon's hand and gloves from the edges of the actuator member, thereby significantly reducing the possibility of the surgeon's gloves becoming torn by contact with the edges of the actuator member.

In accordance with another aspect of the invention, a surgical instrument is provided which includes an elongate handle body, an elongate tubular member having a proximal end fixed to and extending from a distal end of the handle body, an end effector including opposing jaws, at least one of the jaws being movable with respect to the other, a linkage rod slidably positioned in the tubular member and connected at its distal end to the movable jaw of the end effector, a bushing slidably positioned within the handle body, the proximal end of the linkage rod being connected to the bushing, and an improved actuator device which provides easier manipulation, better balance, and easier control for precise manipulation of the jaws of the end effector. The actuator device comprises a resiliently flexible member having a distal end fixed to the handle body and a proximal end connected to the bushing, with the resiliently flexible member being bowed away from the linkage rod, and a lever pivotally connected to the handle body and contacting the resiliently flexible member. Pivoting of the lever toward the handle body causes the resiliently flexible member to be compressed toward the linkage rod, which causes the bushing and linkage rod to move proximally, and which causes movement of the movable jaw of the end effector.

BRIEF DESCRIPTION OF THE DRAWINGS

FIG. 1 is a perspective view of a surgical instrument in accordance with an embodiment of the invention;

FIG. 2 is a side elevational view of the surgical instrument shown in FIG. 1;

FIG. 3 is a perspective view of a surgical instrument in accordance with an alternative embodiment of the invention;

FIG. 4 is an elevation, cross-sectional view of the surgical instrument shown in FIG. 3;

DESCRIPTION OF THE PREFERRED EMBODIMENTS

Figure 5:
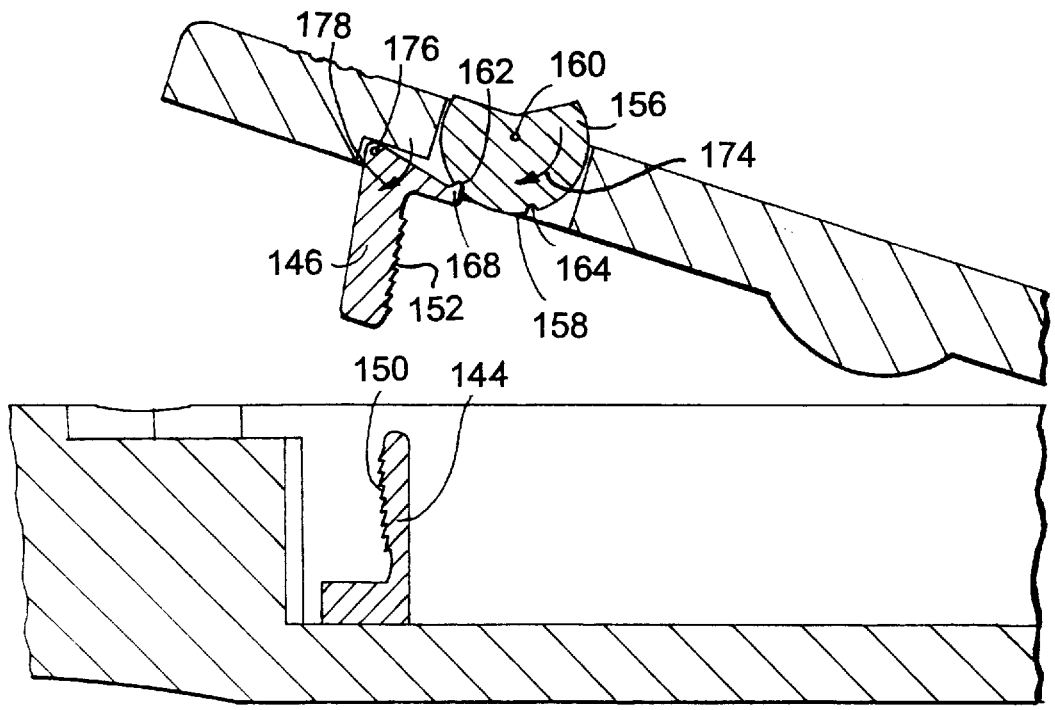
FIG. 5 is an enlarged, fragmentary, elevational, cross-sectional view showing details of a ratchet locking device for the instrument shown in FIGS. 3 and 4 with the lever in the open position.
Figure 6:
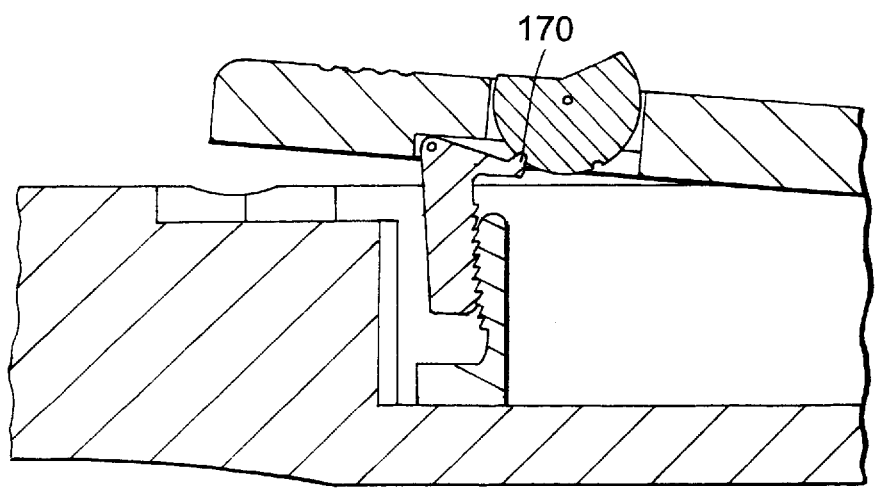
FIG. 6 is an enlarged, fragmentary, elevational, cross-sectional view showing details of the ratchet locking device shown in FIGS. 3–5, with the lever in a closed position.

Shown in the drawings is a surgical instrument 10 including an elongate tubular member 12 having a distal end 14 and a proximal end 16. An end effector 18 is located at the distal end of tubular member 12. A pair of continuous longitudinally opposing actuator members 20 are located near the proximal end of the instrument. Each of the actuator members 20 is resiliently flexible. Each actuator member 20 includes a first, distal end 22 which is connected to the proximal end of the tubular member 12 through a distal connector element 24, and a second, proximal end 26 which is connected to a proximal connector element 28.

The proximal ends 26 of actuator members 20 extend beyond the proximal end of the tubular member 12, and are operably connected to each other through the proximal connector 28. The actuator members 20 are laterally compressible towards each other to effect movement of the proximal and distal connector elements 24, 28 away from each other.

A linkage rod 30 is slidably positioned in the tubular member 12. Linkage rod 30 is connected to the end effector 18 and extends through the tubular member and beyond the proximal end thereof. Linkage rod 30 is operably connected to the resiliently flexible actuator members 20. In particular, as shown in the illustrated embodiment, the proximal end of linkage rod 30 is connected to the proximal connector element 28, which is connected to the proximal ends of each of the actuator members 20. Lateral compression of the flexible actuator members toward each other causes the linkage rod to move in a proximal direction with respect to the tubular member 12, which, in turn, causes the jaws of the end effector to move with respect to each other.

A pair of actuator cover members or levers 32 are located near the proximal end of the instrument 10 adjacent the actuator members 20. Each of the levers 32 has a proximal end and a distal end. The proximal end of each of the levers is pivotally connected to each other or to the proximal connector 28. The distal end of each of the levers extends distally and outwardly away from the longitudinal axis of the tubular member. Each lever 32 generally overlies and contacts a different one of the two actuator members 20. When the levers 32 are pivotally connected to each other, but not pivotally connected to the proximal connector 28, each of the levers 32 are preferably connected with the actuator member 20 which it overlies. Pivoting of levers 32 toward each other causes the flexible actuator members 20 to be compressed toward each other, which causes the linkage rod 30 to move the movable jaw of the end effector 18.

In the illustrated embodiment, end effector 18 includes a fixed jaw 18a and a movable jaw 18b. However, it should be understood that both jaws of the end effector may be movable, as such end effectors are well known in the art and in the literature. Further, it should be understood that the term "jaw" encompasses blades, needle holders, scissors, tissue forceps, smooth holding platforms, etc.

The distal connector 24 and the proximal connector 28 are configured for sliding movement relative to each other along a direction generally defined by the longitudinal axis of the tubular member 12. In the illustrated embodiment, distal connector 24 includes a proximally projecting portion 36, and proximal connector 28 includes a recess 38 in which projecting portion 36 is slidably received to facilitate the sliding movement of the connectors relative to each along the direction generally defined by the longitudinal axis of the tubular member. However, various other types of guide means may be used for maintaining connectors 24 and 28 in proper alignment and to facilitate sliding movement of the connectors with respect to each other along the direction defined by the longitudinal axis of the tubular member.

In operation, pivoting of levers 32 toward each other causes compression of the normally outwardly bowed actuator members 20 toward each other, which, in turn, causes the proximal movement of linkage rod 30 with respect to tubular member 12. Movement of linkage rod 30 is guided slidingly within the hollow portion of tubular member 12. The proximal movement of linkage rod 30 effects proximal movement and rotation of movable jaw 18b about pivot pin 40 and results in movement of movable jaw 18b toward fixed jaw 18a.

Release of levers 32 causes the resiliently flexible actuator members 20 to return to their original open position. This return to the original open position causes the distal movement of linkage rod 30 with respect to tubular member 12 and the return of movable jaw 18b back to the open position.

Levers 32 may be connected to actuator members 20 with conventional fasteners 42, such as rivets, screws, etc.

While the foregoing describes use of the instrument in the field of surgery, the instrument may find appropriate uses in other applications requiring a small, simple jawed tool.

Shown in FIGS. 3 and 4 is an alternative embodiment of the invention. In FIGS. 3 and 4, there is shown a surgical instrument in accordance with a preferred embodiment of the invention. Instrument 110 includes a handle portion generally comprising a handle body 112 having a distal end 114 and a proximal end 116. An elongate tubular member 118 includes a distal end 120 and a proximal end 122. Proximal end 122 of tubular member 118 is fixed to and extends from the distal end 114 of handle body 112. An end effector 124 is located at distal end 120 of tubular member 118. End effector 124 includes opposing jaws 126, 128. In the illustrated embodiment, jaw 126 is fixed, and jaw 128 is movable with respect to jaw 126. More specifically, jaw 128 pivots about pivot axis 130. A linkage rod 132 is slidably positioned in tubular member 118 and is connected at its distal end to movable jaw 128 of end effector 124. Linkage rod 132 extends rearwardly through tubular member 118 and beyond proximal end 122 of tubular member 118. Handle body 112 includes a hollow portion in which a bushing 134 is slidably positioned for reciprocating movement along the longitudinal direction of the handle body. The proximal end of linkage rod 132 is connected to bushing 134.

Surgical instrument 110 includes an improved actuator assembly comprising a resiliently flexible member 136 having a distal end fixed to handle body 112, and a proximal end 140 connected to bushing 134, and a lever 142 pivotally connected to handle body 112. Resiliently flexible member 136 of the illustrated embodiment is a steel leaf spring which is bowed outwardly away from linkage rod 132. Lever 142 is capable of being pivoted toward handle body 112 and contacting resiliently flexible member 136 to cause the resiliently flexible member to be compressed toward linkage rod 132, which in turn causes bushing 134 and linkage rod 132 to move proximally. Proximal movement of linkage rod 132 causes movement of movable jaw 128 of end effector 124.

The ratchet locking device generally comprises a first toothed plate 144 fixed to handle body 112, and a second toothed plate 146 which is pivotally mounted to lever 142. Toothed plate 146 is positioned and normally biased by a spring member 148 into engagement with first toothed plate 144.

Toothed plate 144 and 146 each include a plurality of equally spaced apart teeth which provide a plurality of discrete positions in which the plates can be engaged with each other which correspond with a plurality of discrete positions in which the movable jaw 128 may be positioned with respect to the fixed jaw 126. The teeth of toothed plates 144 an 146 are configured so that the teeth of pivotally mounted toothed plate 146 slide and/or snap over the teeth of fixedly mounted toothed plate 144 as pivotally mounted toothed plate 146 is pivoted against the biasing force of spring member 148 when compressive forces are applied to lever 142 and handle body 112 to pivot them toward each other, and so that the teeth of pivotally mounted toothed plate 146 becomes wedged against the teeth of fixedly mounted toothed plate 144 by the biasing force of spring member 148 when compressive forces ont he lever and the handle body are removed.

With the illustrated instrument 110, a second toothed plate 144' is fixed to handle body 112, and a second toothed plate 146' is pivotally mounted to lever 142. Plate 144' and 146' engage each other in a manner identical to the manner in which plates 144 and 146 engage each other. Plates 144 and 144' are situated on opposite sides of actuator rod 132. Although a single set of engaging toothed plates (144 and 146) may in some cases be adequate, the position of lever 142 with respect to handle body 112 can be more reliably maintained by providing a pair of engaging toothed plates, one on each side of the linkage rod 132. The toothed surfaces 150 and 152 of toothed plate 144 an 146 respectively, are complimentary arcuate surfaces. In particular, toothed surface 150 is slightly convexed and toothed surface 152 has a complimentary concave surface, the radii of the toothed surfaces 150 and 152 being substantially equal. The arcuate surfaces of toothed plates 144 and 146 provide uniform engagement between the toothed plates along the entire range of discrete positions in which the teeth of the plates 144 and 146 become engaged.

Spring 148 in the illustrated embodiment is a coil spring disposed on a pivot axle fixedly connecting plates 146 and 146'. One end of the coil spring is connected to the pivot axle connecting the plates 146 and 146', and the other end is connected to lever 142 to cause plates 146, 146' to be normally biased into engagement with toothed plates 144 and 144'.

A release member 156 is pivotally mounted on lever 142 and rotates about pivot axis 160. Release member 156 includes an arcuate cam surface 158. Recesses 162 and 164 are defined at opposite ends of the arcuate cam surface 158. Toothed plate 146 includes a follower 168 which engages arcuate cam surface 158. Follower 168 includes a pointed projection 170 which stably engages recess 162, whereby toothed plate 146 is retained in a position where it may normally engage toothed plate 144, yet pivot slightly to allow the teeth of toothed plate 146 to slide past the teeth of toothed plate 144. The distance between pivot axis 160 and recess 164 is greater than the distance between pivot 160 and recess 162, so that as release member 156 is rotated in the direction indicated by arrow 174, the tip 170 of follower 168 is disengaged from recess 162, and cam surface 158, having a gradually increasing radius, causes toothed plate 146 to pivot about pivot axis 176 in the direction indicated by arrow 178, and move out of engagement with toothed plate 144. Eventually, pointed projection 170 of follower 168 snaps into recess 164, whereby toothed plate 146 is stably retained in a position out of engagement with toothed plate 144. In the illustrated embodiment, release member 156 includes recesses 162 and 164 which are engaged by a projection 170 on follower 168. However, as an alternative, the release member 156 may be provided with projections at the opposite ends of cam surface 158 and follower 168 may be provided with a recess engaged by projections on opposite ends of cam surface 158.

In operation, release member 156 is pivoted into the position shown in FIG. 5 wherein projection 170 of follower 168 is retained within recess 162, so that toothed plate 146 is held in a position where it will engage toothed plate 144. Lever 142 is then compressed toward handle body 112 and the teeth on toothed plate 146 slide over the teeth on toothed plate 144. At the same time, lever 142 engages resiliently flexible member 136 causing it to flatten out and be compressed inwardly toward the linkage rod 132. This causes bushing 134 to move proximally. Rod 132, which is connected to bushing 134, also moves proximally causing movable end effector 128 to move with respect to jaw 126, i.e., closing the jaws of the end effector. When the jaws of the end effector are at a desired position, the compressive force is applied between lever 142 and handle body 112 are released, and the end effector and lever are retained at the desired position by engagement of the teeth of toothed plate 146 with those of toothed plate 144. Jaws 126 and 128 can be further tightened as desired by further pivoting lever 142 toward handle body 112. The locking device can be released as desired by rotating the release member 156 in the direction indicated by arrow 174 in FIG. 5, until pointed projection 170 of follower 168 becomes wedged within recess 164. In this position, resiliently flexible member 136 urges lever 142 away from handle body 112, while at the same time urging bushing 134 in a distal direction and returning the movable jaw 128 to the open or starting position.

It will be understood that the invention may be embodied in other specific forms without departing from the spirit or central characteristics thereof. The present examples and embodiments, therefore, are to be considered in all respects as illustrated and not restrictive, and the invention is not limited to the details given herein and should be understood as defined by the following claims.

The embodiments of the invention in which an exclusive property of privilege is claimed are defined as follows:

1. A surgical instrument comprising:

an elongate tubular member having a distal end, a proximal end, and a longitudinal axis;

an end effector at the distal end of the tubular member, the end effector including opposing jaws, at least one of the opposing jaws being movable with respect to the other;

a linkage rod having a distal end and a proximal end, the linkage rod being slidably positioned in the tubular member and connected at its distal end to the movable jaw of the end effector, the linkage rod extending rearwardly through the tubular member and beyond the proximal end of the tubular member;

a distal connector fixed to the proximal end of the tubular member;

a proximal connector fixed to the proximal end of the linkage rod;

the distal connector and the proximal connector being configured for sliding movement relative to each other along a direction generally defined by the longitudinal axis of the tubular member;

at least one resiliently flexible actuator member, the actuator member having a distal end and a proximal end, the distal end of the actuator member being operably connected to the tubular member, the flexible actuator member being laterally compressible toward the longitudinal axis of the tubular member; and a lever having a proximal end and a distal end, the proximal end of the lever being pivotally connected to the proximal connector, and the distal end of the lever extending distally and outwardly away from the longitudinal axis of the tubular member, the lever generally overlying and contacting the actuator member, whereby pivoting of the lever toward the longitudinal axis of the tubular member causes the flexible actuator member to be compressed toward the longitudinal axis of the tubular member, which causes the linkage rod to move the movable jaw of the end effector.

2. The surgical instrument of claim 1, wherein one of the connectors includes a projecting portion and the other connector includes a recess which slidably receives the projecting portion of the other connector to facilitate the sliding movement of the connectors relative to each other along the direction generally defined by the longitudinal axis of the tubular member.

3. A surgical instrument comprising:

an elongate tubular member having a distal end, a proximal end, and a longitudinal axis;

an end effector at the distal end of the tubular member, the end effector including opposing jaws, at least one of the opposing jaws being movable with respect to the other;

a linkage rod having a distal end and a proximal end, the linkage rod being slidably positioned in the tubular member and connected at its distal end to the movable jaw of the end effector, the linkage rod extending rearwardly through the tubular member and beyond the proximal end of the tubular member;

a distal connector fixed to the proximal end of the tubular member;

a proximal connector fixed to the proximal end of the linkage rod;

the distal connector and the proximal connector being configured for sliding movement relative to each other along a direction generally defined by the longitudinal axis of the tubular member;

a pair of resiliently flexible longitudinally opposing actuator members, each actuator member having a distal end and a proximal end, the distal end of each actuator member being operably connected to the tubular member, each actuator member being operably connected to the other actuator member at a location proximate their proximal ends, the flexible actuator members being laterally compressible toward each other; and a pair of longitudinally opposing levers, each lever having a proximal end and a distal end, the proximal ends of the levers being connected to each other, and the distal end of each of the levers extending distally and outwardly away from the longitudinal axis of the tubular member, each lever generally overlying a different one of the two actuator members, and each of the levers being connected with the actuator member which it overlies, whereby pivoting of the levers toward each other causes the flexible actuator members to be compressed toward each other, which causes the linkage rod to move the movable jaw of the end effector.

4. The surgical instrument of claim 3, wherein one of the connectors includes a projecting portion and the other connector includes a recess which slidably receives the projecting portion of the other connector to facilitate the sliding movement of the connectors relative to each other along the direction generally defined by the longitudinal axis of the tubular member.

5. A surgical instrument comprising:

an elongate handle body having a distal end and a proximal end;

an elongate tubular member having a distal end and a proximal end, the proximal end of the tubular member being fixed to and extending from the distal end of the handle body;

an end effector at the distal end of the tubular member, the end effector including opposing jaws, at least one of the jaws being movable with respect to the other;

a linkage rod having a distal end and a proximal end, the linkage rod being slidably positioned in the tubular member and connected at its distal end to the movable jaw of the end effector;

a bushing slidably positioned within the handle body, the proximal end of the linkage rod being connected to the bushing;

a resiliently flexible member having a distal end and a proximal end, the distal end of the resiliently flexible member being fixed to the handle body and the proximal end of the resiliently flexible member being connected to the bushing, the resiliently flexible member being bowed away from the linkage rod; and a lever pivotally connected to the handle body and capable of contacting the resiliently flexible member, the resiliently flexible member biasing the lever away from the handle body, whereby pivoting of the lever toward the handle body causes the resiliently flexible member to be compressed toward the linkage rod, which causes the bushing and linkage rod to move proximally, and which causes movement of the movable jaw of the end effector.

6. The surgical instrument of claim 5 further comprising a first toothed plate fixed to one of either the handle body and the lever, a second toothed plate being pivotally mounted to the other of the handle body and the lever, the second toothed plate being normally positioned for engagement with the first toothed plate and normally biased by a spring member into engagement with the first toothed plate, the teeth of the toothed plates being configured so that the teeth of the pivotally mounted toothed plate slide over the teeth of the fixedly mounted toothed plate as the pivotally mounted toothed plate is pivoted against the biasing force of the spring when compressive forces are applied to the lever and the handle body to pivot them toward each other, and so that the teeth of the pivotally mounted toothed plate become wedged against the teeth of the fixedly mounted toothed plate by the biasing force of the spring member when compressive forces on the lever and the handle body are removed, whereby a compressive force can be applied on the lever and the handle body to pivot them toward each other to operate the end effector, and whereby the lever can be locked into one of a plurality of discrete positions to lock the position of the jaws of the end effector relative to each other when compressive forces are removed from the lever and the handle body.

7. The surgical instrument of claim 6 further comprising a release member pivotally mounted to one of either the handle body and the lever, the release member defining an arcuate cam surface and at least one of a projection and a recess at first and second ends of the arcuate cam surface, the second toothed plate including a follower engagable with the arcuate cam surface, the follower including one of a recess or projection which is engagable with the follower or recess at each end of the cam surface to selectively retain the follower at one of the first and second ends of the cam surface, the release member being pivotable between a first position wherein the follower is retained at the first end of the cam surface and wherein the teeth of the second toothed plate engage the teeth of the first toothed plate, and a second position when the follower is retained at the second end of the cam surface and wherein the second toothed plate is pivoted away from engagement with the first toothed plate by the release member whereby the laterally opposing members are urged away from each other by the resilient member.

8. The surgical instrument of claim 7, wherein the toothed plates have complimentary arcuate toothed surfaces.

* * * * *